US006875855B1

(12) United States Patent
Roberts et al.

(10) Patent No.: US 6,875,855 B1
(45) Date of Patent: Apr. 5, 2005

(54) NUCLEIC ACID AND AMINO ACID SEQUENCES OF HEMOGLOBIN-RESPONSE GENES IN *CANDIDA ALBICANS* AND THE USE OF REAGENTS DERIVED FROM THESE SEQUENCES IN THE DIAGNOSIS OF DISSEMINATED *CANDIDA ALBICANS* INFECTION

(75) Inventors: David D. Roberts, Bethesda, MD (US); Sizhuang Steve Yan, Bethesda, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/258,634

(22) Filed: Feb. 26, 1999

(51) Int. Cl.[7] ............................................. C07H 21/04
(52) U.S. Cl. ................ 536/23.7; 435/252.3; 435/254.2; 435/254.22; 435/320.1; 424/254.2; 424/320.1; 536/24.3
(58) Field of Search ..................... 435/252.3; 424/254.2, 424/254.22, 320.1; 536/23.7, 24.3

(56) References Cited

U.S. PATENT DOCUMENTS 5,677,172 A * 10/1997 Makarow
5,874,217 A * 2/1999 Halverson et al.
5,998,164 A * 12/1999 Li et al.

OTHER PUBLICATIONS

Overbeek (1994, "Factors affecting transgenic animal production," Transgenic animal technology, pp. 96–98).*
Wall, 1996 Theriogenology, vol. 45, pp. 57–68.*
Houdebine, 1994, J. Biotech. vol. 34, pp. 269–286.*
Kappell, 1992, Current Opinions in Biotechnology, vol. 3, pp. 548–552.*
Cameron, 1997, Molec. Biol. 7, pp. 253–265, specifically p. 256.*
Niemann, 1997, Transg. Res. 7, pp. 73–75.*
Mullins (1993, Hypertension, vol. 22, pp. 630–633).*
Mullins (1990, Nature, vol. 344, 541–544).*
Hammer (1990, Cell, vol. 63, 1099–1112).*
Mullins, 1989, EMBO J., vol. 8, pp. 4065–4071.*
Taurog, 1988, Jour. Immunol., vol. 141, pp. 4020–4023.*
Ghadessy et al. (Journal of Biological Chemistry vol. 271, No. 41, pp. 25575–25581, 1996).*
Lathe, Journal of Molecular Biology, 1985, vol. 183, No. 1, pp. 1–12.*
Primer, random pd(N)6, Boehringer Mannheim, Biochemicals, 191 Catalog, 1991.*
Pohl T.M. "S. cerevisiae chromosome IV reading frame ORF YDL166c" *Embl. Database Entry SCYDL166C, Accession No. Z74214* (1996).
Murakami Y. et al. "Cofactor: pyridoxal phosphate." *Swissprot Database Entry AFDO_Yeast, Accession No. P43567* (1995).

* cited by examiner

Primary Examiner—Lynette R. F. Smith
Assistant Examiner—Robert A. Zeman
(74) Attorney, Agent, or Firm—Liniak, Berenato & White; Jeffrey I. Auerbach

(57) ABSTRACT

Three hemoglobin-response genes in the pathogenic yeast *Candida albicans* are disclosed. The expression of these genes is specifically induced when the organism is exposed to hemoglobin during disseminated infections. The invention relates to the nucleic acid and amino acid sequences of these hemoglobin-response genes. The invention also relates to diagnostic methods, kits and compositions which employ the nucleic acid and amino acid sequences of the invention.

20 Claims, 10 Drawing Sheets

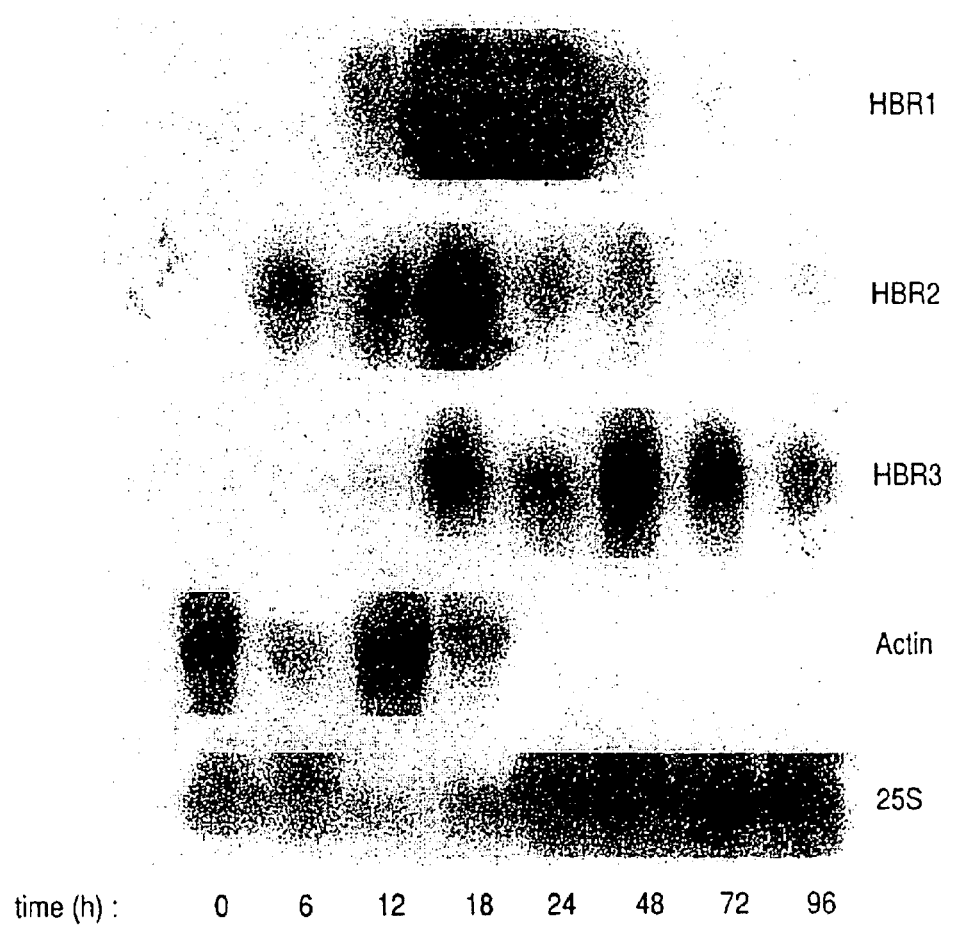

NUCLEIC ACID AND AMINO ACID SEQUENCES OF HEMOGLOBIN-RESPONSE GENES IN *CANDIDA ALBICANS* AND THE USE OF REAGENTS DERIVED FROM THESE SEQUENCES IN THE DIAGNOSIS OF DISSEMINATED *CANDIDA ALBICANS* INFECTION

FIELD OF THE INVENTION

The present invention relates to the nucleic acid and amino acid sequences of hemoglobin-response genes in the pathogenic yeast *Candida albicans*. More specifically, as these hemoglobin-response genes are specifically induced when the organism initiates disseminated infections, the invention relates to diagnostic methods, kits and compositions which employ the nucleic acid and amino acid sequences of the invention.

BACKGROUND OF THE INVENTION

*Candida albicans* is a pathogenic yeast commonly found in the intestinal digestive tract of healthy individuals. *Candida albicans* is usually limited to the intestines of the digestive tract, where it causes harmless commensal colonization. However, *Candida albicans* can also infect various parts of the body such as the skin, nails, mouth, vagina, airways and bloodstream, causing both superficial and disseminated infections. Candidiasis refers to chronic infections by *Candida albicans*. Candidiasis is often fatal among patients with compromised immune system such as organ and bone marrow transplant recipients, human immunodeficiency virus carriers, and neonates. Candidiasis has become more common due to its increasing incidence in immunocompromised patients (5–10) and its development of resistance toward the limited range of available antifungal agents (11–15).

Diagnostic kits for the detection of commensal colonization by *Candida albicans* in humans are currently available. However, as approximately 60% of healthy individuals harbor *Candida albicans* in their gastrointestinal tract, it is important to identify specific marker genes which can differentiate a harmless commensal colonization from a life-threatening blood-borne disseminated infection.

Recently, hemoglobin, a component of blood, has been identified as a host factor that specifically induces increased adhesion of *C. albicans* blastoconidia to fibronectin (20, 21). Fibronectin is a major component of the host extracellular matrix that may play an important role in the initiation and dissemination of *C. albicans* infection. Hemoglobin has also been shown to induce changes in expression of several proteins exposed on the yeast cell wall, including a 55 kDa protein that binds fibronectin (21, 22). Thus, the identification and characterization of hemoglobin-response genes may be useful in differentiating a harmless commensal colonization from a life-threatening blood-borne disseminated infection.

Recognition of host factors by pathogens may also initiate adaptive responses that facilitate infection. Successful pathogens have developed bidirectional signal transduction pathways to achieve environments in their hosts that are optimal for colonization and growth of the invading microorganisms (1–3). Following contact with the host, pathogens produce factors that alter gene expression or function in host cells to facilitate infection (2). Conversely, pathogenic microorganisms must also alter their gene expression in response to specific signals from the host (1, 3, 4). Thus, identification of host factor-response genes could lead to new therapeutic approaches to prevent or treat these infections.

SUMMARY OF THE INVENTION

The present invention relates to the isolation and characterization of the nucleic acid sequences of three hemoglobin-response genes in the pathogenic yeast *Candida albicans*. The expression of these genes is specifically induced when the organism is exposed to hemoglobin during disseminated infections. In particular, the present invention relates to these nucleic acid sequences and to the encoded amino acid sequences.

The invention also relates to vectors comprising the nucleic acids of this invention and to cultured host cells comprising these vectors.

The invention also relates to proteins or peptide fragments thereof encoded by the nucleic acids of this invention.

The invention further relates to methods for producing the proteins or peptide fragments of the invention.

The invention also relates to antibodies which have specific binding affinity to the proteins or peptide fragments encoded by the hemoglobin-response genes of the invention.

The invention also relates to the use of the nucleic acid sequences, proteins or peptide fragments or antibodies of the invention in methods for diagnosing disseminated *Candida albicans* infection in a mammal. In one embodiment, the method utilizes the proteins or peptide fragments of the invention to detect antibodies which have specific binding affinity to the proteins or peptide fragments of this invention in a mammal. In another embodiment, the method uses the antibodies of this invention to detect the proteins or peptide fragments encoded by the hemoglobin-response genes. In yet another embodiment, the method comprising analyzing the nucleic acid of a mammal for the presence of hemoglobin-response gene sequences using the nucleic acid sequences of this invention.

The invention also provides kits for the diagnosis of disseminated *Candida albicans* infection in a mammal. In one embodiment, the kit contains at least one proteins or peptide fragment of this invention useful for the detection of antibodies specific for the proteins or peptide fragments of the invention. The invention also relates to kits for detecting the proteins or peptide fragments of this invention, wherein the kit comprises at least one antibody of this invention. In another embodiment, the kit comprises nucleic acid molecules having sequences useful as hybridization probes in determining the presence or absence of the nucleic acids of the hemoglobin-response genes of this invention. In yet another embodiment, the kit comprises nucleic acids having sequences useful as primers for nucleic acid sequence-based amplification (NASBA) analysis of RNA for the presence of the hemoglobin-response genes in a mammal.

The invention further relates to isolated and substantially purified nucleic acids, proteins, peptide fragments and antibodies of the invention.

The invention also relates to compositions comprising one or more of the nucleic acids, proteins, peptide fragments and antibodies of the invention.

BRIEF DESCRIPTION OF THE FIGURES

FIGS. 1A–E. Differential display polymerase chain reaction (PCR) identification of iron- and hemoglobin-induced genes. (1A) Hemoglobin-induced gene transcripts (H) were compared to cDNA from non-induced controls (C) and ferrous sulfate-induced cultures (F) amplified using three arbitrary primers (lanes 1–3). (1B) Specificity of HBR1 rRNA induction by hemoglobin. Total RNA from cells grown in yeast nitrogen base (YNB), YNB+ferrous sulfate (iron), YNB+1 mg/ml hemoglobin (Hb), or induced to form hyphae were hybridized with DNA probes for HBR1 or pyruvate carboxylase 2 (control) in a Northern analysis. (1C) Kinetics of induction of mRNAs by hemoglobin. HBR1, HBR2, HBR3, actin, or 25S ribosomal RNA were hybridized with the respective probes. Temperature-dependence for HBR3 (1D) and HBR1 induction (1E). Total RNA was analyzed by Northern blots and quantified by PhosphorImager analysis using ImageQuant (Molecular Dynamics, Sunnyvale, Calif.). The fold-induction in a representative experiment is presented for iron-(Fe) or hemoglobin-induced cultures (Hb) relative to uninduced control cultures grown at the respective temperatures.

DETAILED DESCRIPTION OF THE INVENTION

Figure 1A:
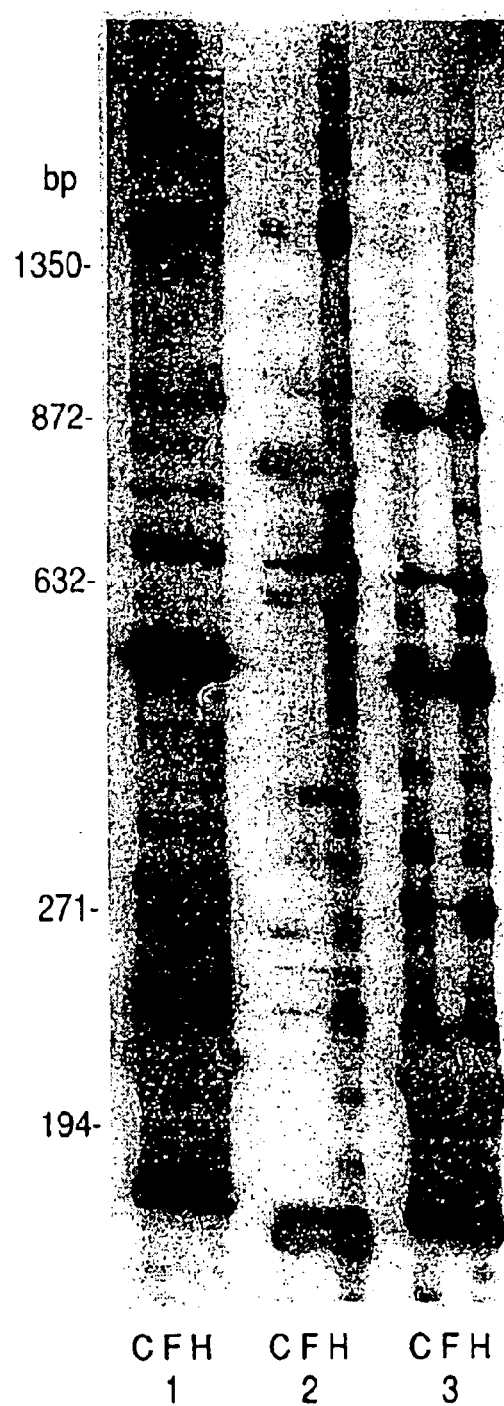

The present invention relates to the isolation and characterization of three hemoglobin-response genes in the pathogenic yeast Candida albicans. The expression of these genes is specifically induced when the organism is exposed to hemoglobin during disseminated infections. These hemoglobin-response genes, designated HBR1, HBR2 and HBR3, were identified by screening a Candida albicans genomic library using DNA from EST clones (SEQ ID NOS: 11–13). The EST clones comprise sequences which exhibited increased expression in Candida albicans cultures containing hemoglobin and were obtained using random arbitrary primer-polymerase chain reaction.

The present invention therefore relates to nucleic acid molecules having the sequences of any one of the hemoglobin-response genes of this invention (nucleic acid sequences are shown in SEQ ID NOS: 1–3; amino acid sequences shown in SEQ ID NOS: 4 and 5 are encoded by SEQ ID NOS: 1 and 2, respectively) as well as fragments (or partial sequences) thereof. Partial sequences may be obtained by various methods, including restriction digestion, PCR amplification and direct synthesis.

The invention also relates to nucleic acids having complementary (or antisense) sequences of the sequence shown in SEQ ID NOS: 1–3, as well as fragments thereof.

The present invention also relates to nucleic acids derived from the nucleic acid sequences shown in SEQ ID NOS: 1–3.

The present invention also relates to vectors comprising the nucleic acids of the invention, where suitable vectors include, but are not limited to, any vector that is capable of carrying and expressing the nucleic acids of the invention in prokaryotic or eukaryotic host cells.

The present invention therefore also relates to host cells comprising the vectors of the invention.

The expression of the hemoglobin-response genes of the invention is specifically induced when Candida albicans is exposed to hemoglobin during disseminated infections. Therefore, these hemoglobin-response genes provide a useful tool for the diagnosis of disseminated Candida albicans infection in a mammal.

The present invention therefore also relates to a method for diagnosing disseminated Candida albicans infection in a biological sample using the nucleic acids of this invention.

Biological samples appropriate for the diagnostic assays of this invention include, but are not limited to, serum, and tissue samples from a biopsy obtained from a mammal.

The word "mammal" as used throughout the specification, includes, but is not limited to, humans.

In one embodiment, the diagnostic method involves analyzing DNA of a biological sample. DNA can be isolated by methods well known in the art.

The methods for analyzing DNA for diagnosing disseminated Candida albicans infection include Southern blotting, and dot and slot hybridization.

The nucleic acid sequences used in the detection methods set forth above are derived from any one of the nucleic acid sequences shown in SEQ ID NOS:1–3. When used as a hybridization probe, the size of the sequence used is usually at least 20 bases long, preferably 200–500 bases long.

The nucleic acid probes of this invention may be DNA or RNA. Nucleic acids can be synthesized using any of the known methods of nucleotide synthesis, or they can be isolated fragments of naturally occurring or cloned DNA.

The nucleic acid probes can be labeled using methods known to one skilled in the art. Such labeling techniques can include radioactive labels, biotin, avidin, enzymes and fluorescent molecules.

The nucleic acid probes used in the detection methods set forth above are derived from sequences substantially homologous to any one of the sequences shown in SEQ ID NOS:1–3, or its complementary sequence. By "substantially homologous", as used throughout the specification to describe the nucleic acid sequences of the present invention, is meant a high level of homology between the nucleic acid sequence and any one of the sequences of SEQ ID NOS: 1–3, or its complementary sequence. Preferably, the level of homology is in excess of 80%, more preferably in excess of 90%, with a preferred nucleic acid sequence being in excess of 95% homologous with a portion of any one of the sequences of SEQ ID NOS:1–3, or its complement.

In another embodiment of the invention, the diagnostic method comprises analyzing the RNA isolated from a biological sample for detecting the presence of disseminated *Candida albicans* infection. RNA can be isolated by methods well known in the art.

The methods for analyzing the RNA for diagnosing disseminated *Candida albicans* infection include, but are not limited to, Northern blotting, dot and slot hybridization, filter hybridization, RNase protection, reverse-transcription polymerase chain reaction (RT-PCR), and nucleic acid sequence-based amplification (NASBA). A preferred method is NASBA. This method utilizes AMV reverse transcriptase, Rnase H and T7 RNA polymerase. In this method, the RNA can be transcribed to a first stand cDNA using AMV reverse transcriptase and a first nucleic acid probe. The first nucleic acid probe typically comprises a T7 polymerase promoter sequence in addition to a nucleic acid sequence derived from the nucleic acids of this invention. A second strand cDNA is then synthesized with a second nucleic acid probe derived from the nucleic acids of this invention utilizing the DNA-dependent DNA polymerase activity of the AMV reverse transcriptase. Once the double-stranded DNAs are synthesized, they serve as templates for the synthesis of antisense and sense RNAs in a reaction utilizes T7 RNA polymerase. The "cyclic phase" of the reaction begins as the newly synthesized RNA molecules serve as templates for the synthesis of additional first and second strand cDNA molecules.

The size of the nucleic acid probes used as primers in the amplification methods set forth above is usually at least 7 bases long, preferably 20–40 bases long.

The amplification products obtained from the amplification methods can be detected either directly or indirectly. In one embodiment, direct detection of the amplification products is carried out via labeling of the nucleic acid probes. Labels suitable for labeling the nucleic acid probes of the present invention are known to one skilled in the art and include radioactive labels, biotin, avidin, enzymes and fluorescent molecules.

In another embodiment, unlabelled amplification products can be detected via hybridization with labeled nucleic acid probes in methods known to one skilled in the art, such as dot or slot blot hybridization or filter hybridization.

The present invention also relates to diagnostic kits comprising the nucleic acid probes of this invention. The diagnostic kits may include other reagents and materials required for the hybridization or amplification protocols in addition to the probes.

The present invention also relates to recombinant methods of using the nucleic acids of the invention to produce proteins or peptide fragments.

In one embodiment, the method comprises:
(a) preparing of a nucleic acid capable of directing a host cell to produce a protein or peptide fragment encoded by any one of the sequences shown in SEQ ID NOS:1–3;
(b) cloning the nucleic acid into a vector capable of being transferred into and replicated in a host cell;
(c) transferring the vector containing the nucleic acid into a host cell capable of expressing the protein or peptide fragment;
(d) growing the host under conditions appropriate for expression of the protein or peptide fragment; and
(e) harvesting the protein or peptide fragment.

The vectors contemplated for use in the present invention include any vectors into which a nucleic acid sequence as described above can be inserted, along with any preferred or required sequences, and which vector can then be subsequently transferred into a host cell and, preferably, replicated in such cell.

The present invention also relates to proteins or peptide fragments encoded by and/or derived from the nucleic acids of this invention. These proteins or peptide fragments may be natural, synthetic or produced by recombinant methods. They can be obtained as a crude lysate or can be purified by standard protein purification procedures known in the art which may include differential precipitation, molecular sieve chromatography, ion-exchange chromatography, isoelectric focusing, gel electrophoresis and affinity and immunoaffinity chromatography. The present invention also relates to compositions comprising one or more of the proteins or peptide fragments of the invention.

A recombinant or derived proteins or peptide fragments is not necessarily translated from a designated nucleic acid sequence; it may be generated in any manner, including for example, chemical synthesis, or expression of a recombinant expression system.

It should be noted that the nucleotide sequences described herein represent one embodiment of the present invention. Due to the degeneracy of the genetic code, it is to be understood that numerous choices of nucleotides may be made that will lead to a sequence capable of directing production of the proteins or peptide fragments set forth above. As such, nucleic acid sequences which are functionally equivalent to the sequences described herein are intended to be encompassed within the present invention. For example, preferred codons which are appropriate to the host cell may be used.

The present invention further relates to the use of the proteins or peptide fragments of the invention as diagnostic agents.

In one embodiment, the proteins or peptide fragments of the invention can be used in immunoassays for detecting the presence of antibodies against proteins or peptide fragments encoded by any one of the hemoglobin-response genes in a biological sample and for diagnosing disseminated *Candida albicans* infection in a biological sample.

In a preferred embodiment, test serum is reacted with a solid phase reagent having a surface-bound proteins or peptide fragments of this invention as an antigen. The solid surface reagent can be prepared by known techniques for attaching proteins or peptide fragments to solid support material. These attachment methods include non-specific adsorption of the proteins or peptide fragments to the support or covalent attachment of the proteins or peptide fragments to a reactive group on the support. Unbound serum components are removed by washing and the antigen-antibody complex is reacted with a secondary antibody such as labeled anti-human antibody. The label may be an enzyme which is detected by incubating the solid support in the presence of a suitable fluorimetric or colorimetric reagent. Other detectable labels may also be used, such as radiolabels or colloidal gold, and the like.

Immunoassays of the present invention may be a radioimmunoassay, Western blot assay, immunofluorescent assay, enzyme immunoassay, chemiluminescent assay, immunohistochemical assay and the like. Standard techniques for ELISA are well known in the art.

The present invention further relates to diagnostic kits comprising the proteins or peptide fragments of this invention. Such diagnostic kits may include other reagents and materials required for the immunoassays.

In another embodiment, the proteins or peptide fragments of the invention can be used to prepare antibodies against proteins or peptide fragments encoded by any one of the hemoglobin-response genes that are useful in diagnosis.

The term "antibodies" is used herein to refer to immunoglobulin molecules and immunologically active portions of immunoglobulin molecules. Exemplary antibody molecules are intact immunoglobulin molecules, substantially intact immunoglobulin molecules and portions of an immunoglobulin molecule, including those portions known in the art as Fab, Fab', F(ab')$_2$ and F(v) as well as chimeric antibody molecules.

An antibody of the present invention is typically produced by immunizing a mammal with an immunogen. In one embodiment, the immunogen contains one or more proteins or peptide fragments of the invention, or a structurally and/or antigenically related molecule, to induce, in the mammal, antibody molecules having immunospecificity for the immunizing peptide or peptides. The peptide(s) or related molecule(s) may be monomeric, polymeric, conjugated to a carrier, and/or administered in the presence of an adjuvant. In another embodiment, the immunogen contains one or more nucleic acids encoding one or more proteins or peptide fragments of the invention, or one or more nucleic acids encoding structurally and/or antigenically related molecules, to induce, in the mammal, the production of the immunizing proteins or peptides.

The antibody molecules of the present invention may be polyclonal or monoclonal. Monoclonal antibodies may be produced by methods known in the art. Portions of immunoglobulin molecules may also be produced by methods known in the art.

The presence of the antibodies of the invention can be determined by, but are not limited to, the various immunoassays described above.

The present invention also relates to the use of the antibodies of the invention for diagnosing disseminated *Candida albicans* infection in a biological sample. The antibodies can be used as an in vitro diagnostic agent in biological samples in standard immunoassay protocols. Preferably, the assays which use the antibodies to diagnosing disseminated *Candida albicans* infection in a sample involve contacting the sample with at least one of the antibodies under conditions which will allow the formation of an immunological complex between the antibody and the *Candida albicans* antigen that may be present in the sample. The formation of an immunological complex if any, is then detected and measured by suitable means. Such assays include, but are not limited to, radioimmunoassays (RIA), ELISA, indirect immunofluorescence assay, Western blot and the like. The antibodies may be labeled or unlabeled depending on the type of assay used. Labels which may be coupled to the antibodies include those known in the art and include, but are not limited to, enzymes, radionucleotides, fluorogenic and chromogenic substrates, cofactors, biotin/avidin, colloidal gold and magnetic particles. Modification of the antibodies allows for coupling by any known means to carrier proteins or peptides or to known supports, for example, polystyrene or polyvinyl microtiter plates, glass tubes or glass beads and chromatographic supports, such as paper, cellulose and cellulose derivatives, and silica.

The present invention further relates to diagnostic kits comprising the antibodies of this invention. Such diagnostic kits may include other reagents and materials required for the immunoassays.

The present invention further relates to antisense nucleic acids designed to inhibit the translation of proteins or peptide fragments encoded by the hemoglobin-response genes of the invention. The antisense nucleic acids are complementary to *Candida albicans* mRNAs encoding the proteins or peptides fragments of this invention. The antisense nucleic acids may be in the form of synthetic nucleic acids or they may be encoded by a nucleotide construct.

Figure 6:
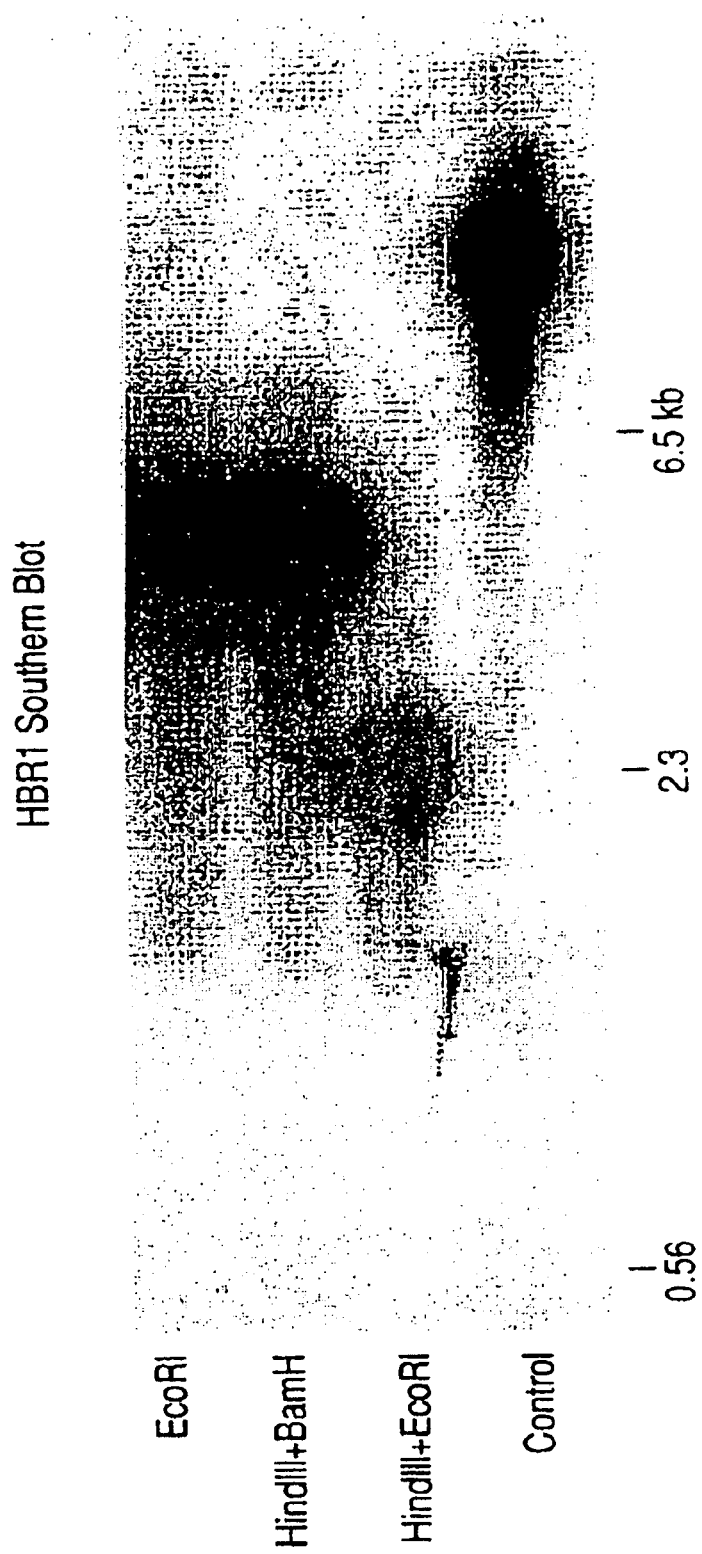
FIG. 6. Identification of HBR gene copy number from genomic DNA by Southern blot. Genomic DNA isolated from Candida albicans were either undigested (control), or digested with EcoRI, HindIII and BamHI, and HindIII and EcoRI, separated by electrophoresis, and immobilized onto membrane. Hybridization was performed using HBR1 gene as a probe in QuikHyb solution (Stratagene, La Jolla, Calif.) at 68° overnight.

As homologous of the hemoglobin-response genes of the invention can be readily obtained using hybridization conditions such as the one described in FIG. 6, it is to be understood that the invention also encompasses the homologous of these hemoglobin-response genes in other pathogenic species of *Candida* such as *Candida glabrata, Candida guilleirmondii, Candida kruzei, Candida tropicalis,* and *Candida trachomatis*.

The present invention will now be described by way of examples, which are meant to illustrate, but not limit, the scope of the invention.

All of the references cited herein are hereby incorporated by reference.

EXAMPLES

Materials and Methods

Cell Culture

The wildtype *C. albicans* strain 44807 (American Type Culture Collection) was inoculated into 4×yeast nitrogen base (YNB) medium with or without 62 μM (expressed as Fe equivalents) hemoglobin or ferrous sulfate and grown at 26° C. for 48 hr (20–22, 24). Under these growth conditions, no germination was found upon microscopic examination. For induction of the hyphal form of *C. albicans*, cells grown in YNB were resuspended into RPMI 1640 supplemented with 2 mM glutamine in the absence of hemoglobin and incubated 2 h at 37° C. with shaking at 250 rpm. A two hour incubation converted nearly 100% of candidal cells to hyphae or pseudohyphae by microscopic examination.

The wildtype *C. albicans* strain SC5314 (wildtype parental isolate for all mutant strains), and the URA3+ homozygous mutants cph1/cph1 (Can16, ura3::imm434/ura3::imm434 cph1::hisG/cph1::hisG-URA3-hisG), hst7/hst7 (Can18, ura3::imm434/ura3::imm434 hst7::hisG/hst7::hisG-URA3-hisG), cst20/cst20 (Can 26, ura3::imm4341/ura3::imm434 cst20::hisG/cst20::hisG-URA3-hisG), the ura3 mutant CAI4, and the corresponding ura3/URA3 parent strain CAF2 (29) were also used in the experiments.

Total RNA Preparation and Differential Expression Display

Cells were collected, washed with TE buffer, pH 7.4, and mixed with RNAzol or Ultraspec RNA (Biotecx Laboratories, Houston, Tex.) in the presence of baked glass beads on ice. The cells were disrupted using a mini Bead-Beater for an accumulated period of 5 min, with cooling on ice at 1 min intervals, followed by briefly vortexing in the presence of chloroform (20% of total volume). The extracted total RNA was precipitated and dried. Differentially expressed genes were identified by RNA arbitrarily primed PCR (RAP-PCR) (Stratagene, La Jolla, Calif.). The first strand cDNA was synthesized with MMLV-reverse transcriptase using arbitrary primers, followed by a PCR with a higher stringency in the presence of [$\alpha$-$^{32}$P]dATP according to the manufacturer's instructions. Five distinct arbitrary primers were used: AATCTAGAGCTCCTCCTC (SEQ ID NO:6); AATCTAGAGCTCCA-GCAG (SEQ ID NO:7); AATCTAGAGCTCTCCTGG (SEQ ID NO:8); AATCTAGAG-CTCTCCAGC (SEQ ID NO:9); and AATCTAGAGCTCCCTCCA (SEQ ID NO:10).

Nucleotide Sequencing, Northern Hybridization and Genomic Library Screening

DNA from positive RAP-PCR bands were extracted, amplified and subcloned into a TA cloning vector (Invitrogen, Carlsbad, Calif.). Expressed sequence tag (EST) sequences were determined by automated sequencing on an ABI Prism sequencer, model 377, using fluorescent terminators. The sequences were verified by multiple sequencing reactions on each strand. Differential expression of the genes induced by hemoglobin was confirmed by Northern hybridization with DNA from each clone as probe. Probe DNA was labeled with Prime-It RmT (Stratagene, La Jolla, Calif.). Total RNAs (25 $\mu$g/lane) from C. albicans prepared under various conditions were separated on 1% agarose gels containing 6.2% formaldehyde and transferred to GeneScreen Plus membrane (NEN Research Products, Boston, Mass.). Hybridization was performed with the corresponding probes in a buffer containing 0.5% BSA, 0.1% SDS, 1 mM EDTA and 0.5 M $NaH_2PO_4$, pH 7.4 at 65° C. overnight.

The C. albicans C9 genomic library was obtained from the National Institutes of Health AIDS Research and Reference Reagent Program, Division of AIDS, NIAID, NIH. E. coli harboring the C9 genomic library were diluted and plated onto ampicillin-containing plates. Colonies were lifted onto nitrocellulose membranes, followed by in-situ hybridization using standard procedures. The genomic clones for HBR1, HBR2, and HBR3 were obtained by screening the library using DNA fragments acquired from differential display.

Chromosomal Mapping

For chromosome mapping, HpaI fragments of HBR1 (4 kb) and HBR2 (5 kb) and the HindIII/ScaI fragment of HBR3 (1.8 kb) from the gene inserts in plasmid 1041 were labeled with $^{32}$P dATP and probed to chromosome separations of Candida albicans strains 1006 and WO-1, and to SfiI digested chromosomal DNA of strain 1006 (25).

In Vivo Induction of Hemoglobin-response Genes

C. albicans (ATCC 44807) organisms from stock isolates were streaked onto Sabouraud glucose agar plates, and incubated at 37° C. for 24 h. Three to five discrete colonies were then inoculated into 50 ml of Emmon's modified Sabouraud broth, pH 7.0 and incubated at 37° C. for 16 h on a shaking incubator at 80 rpm. The Candida suspension was then centrifuged, washed three times in sterile 0.9% NaCl, counted by hemacytometer, and diluted to 6.4×10$^8$ CFU/mL concentration of blastoconidia Inoculum size was confirmed by plating serial dilutions onto SGA check plates. A volume of 1000 $\mu$l of this suspension was mixed with 1000 $\mu$l of heparinized whole blood from each rabbit. The final inoculum was 1×10$^8$ CFU/ml.

Three New Zealand white rabbits weighing 2.5 to 3.5 kg were individually housed and provided food and water in accordance with National Institutes of Health and American Association for the Accreditation of Laboratory Animal Care guidelines on care and use of laboratory animals. A silastic venous catheter was inserted under sterile operative conditions, as previously described in each rabbit (26). The central venous catheter permitted C. albicans to be incubated with heparinized whole blood within the anterior vena cava of the rabbit. Following incubation for five hours, 1.0 ml of blood was withdrawn through the catheter in order to retrieve the C. albicans for extraction of fungal RNA. This incubation process was repeated with a new inoculum of C. albicans once each day for three consecutive days. Candida cells were recovered from whole blood by hypotonic lysis of the erythrocytes followed by centrifugation. Total RNA was prepared as above and analyzed by Northern blotting.

Tyrosine Phosphorylation Assays

Equal amounts of Candida cells grown in the presence or absence of 0.1% hemoglobin for 30 to 180 min were washed, suspended in RIPA buffer (50 mM Tris HCl, pH 7.4, 150 mM NaCl, 1% NP-40, 0.5% sodium deoxycholate, 1 mM EGTA, 1 mM NaF, 1 mM sodium orthovanadate, 10 $\mu$g/ml antipain, pepstatin, chymostatin, leupeptin, aprotinin, soybean trypsin inhibitor, 1 mM PMSF) with 0.5 mm glass beads, and broken using a Bead-Beater as described above. Clarified lysates from equal cell numbers were separated by SDS gel electrophoresis on a 4–15% gradient acrylamide gel (BioRad) and transferred to nitrocellulose. Tyrosine phosphorylation was detected using RC-20 antibody (Transduction Laboratories), peroxidase-conjugated anti-mouse IgG, and ECL reagent (Amersham).

Example 1

Hemoglobin Specifically Alters Expression of Multiple Genes

To understand the basis for the altered expression of cell surface proteins in C. albicans cells grown in the presence of hemoglobin (22), random arbitrary primed-PCR was used to examine changes in mRNA expression in C. albicans induced by hemoglobin. Expression patterns were compared to untreated control cells or cells treated with equivalent concentrations of ferrous sulfate to exclude those mRNAs induced by iron that may be released by degradation of the added hemoglobin (FIG. 1A). Some of the differentially expressed PCR products were induced by either inorganic iron or hemoglobin (FIG. 1A, **), whereas others were specifically induced (*) or inhibited (−) by hemoglobin.

cDNAs for the differentially expressed genes were amplified, subcloned into a TA cloning vector, and sequenced. A total of 33 ESTs that exhibited increased expression in cultures supplemented with hemoglobin but not in cultures supplemented with an equivalent molar concentration of an inorganic ferrous salt were cloned and sequenced. By sequence comparison and homology searches against GenBank and the Saccharomyces genome database, 7 of the 33 ESTs were identified as ESTs from carboxypeptidase Y, and the remainder represented ESTs from 21 discreet mRNAs.

Figure 1B:
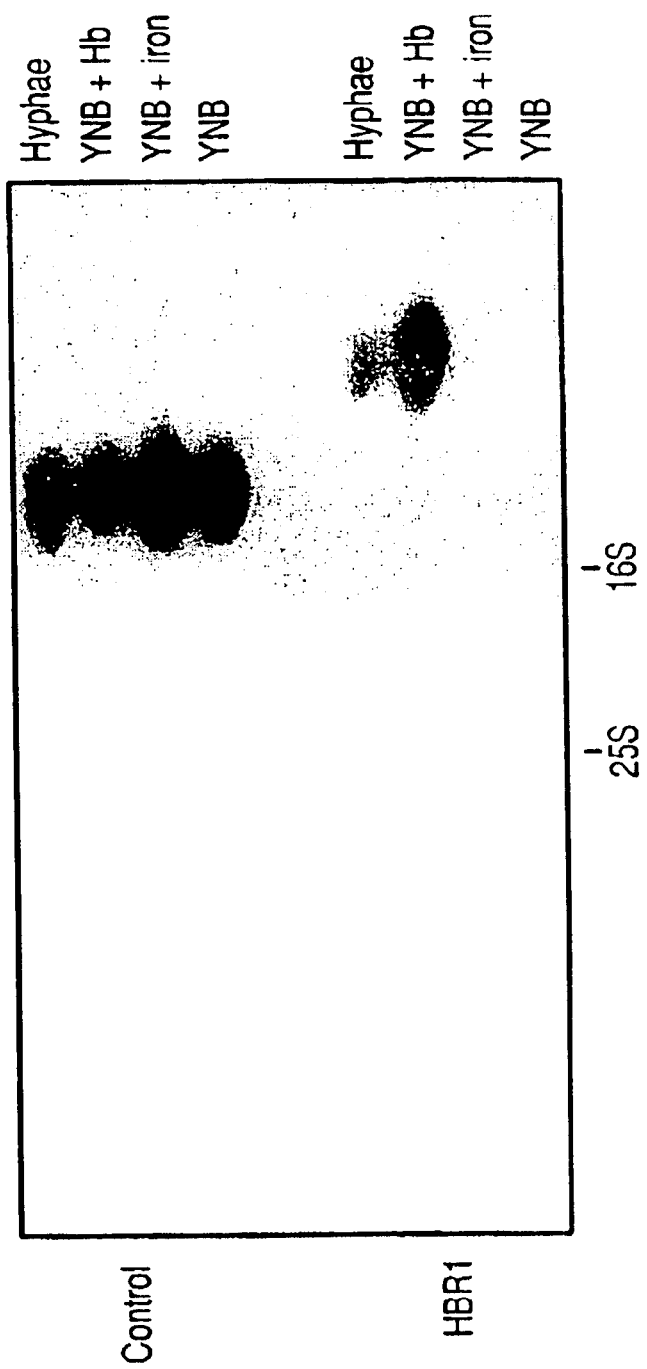

The latter clones and representative carboxypeptidase Y clones were screened by Northern blotting for differential induction by hemoglobin, inorganic iron, or hyphal differentiation. Carboxypeptidase Y is induced both late in hyphal differentiation (27) and by hemoglobin (Table 1). Of the remaining clones, 5 were validated by Northern blots to be induced preferentially by hemoglobin compared to mRNAs from cells treated with inorganic iron or cells induced to form hyphae in RPMI 1640 supplemented with glutamine at 37° C. (FIG. 1B and Table 1).

Figure 1D:
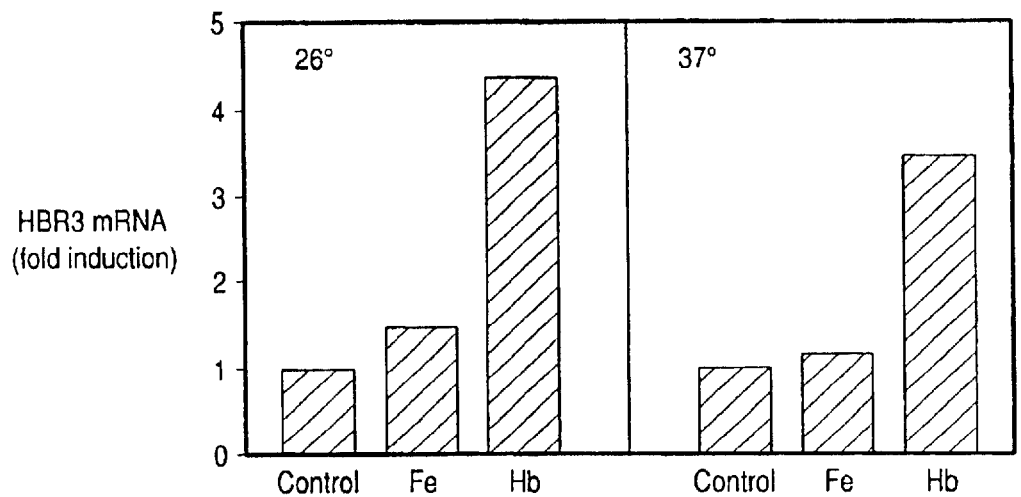
Figure 1E:
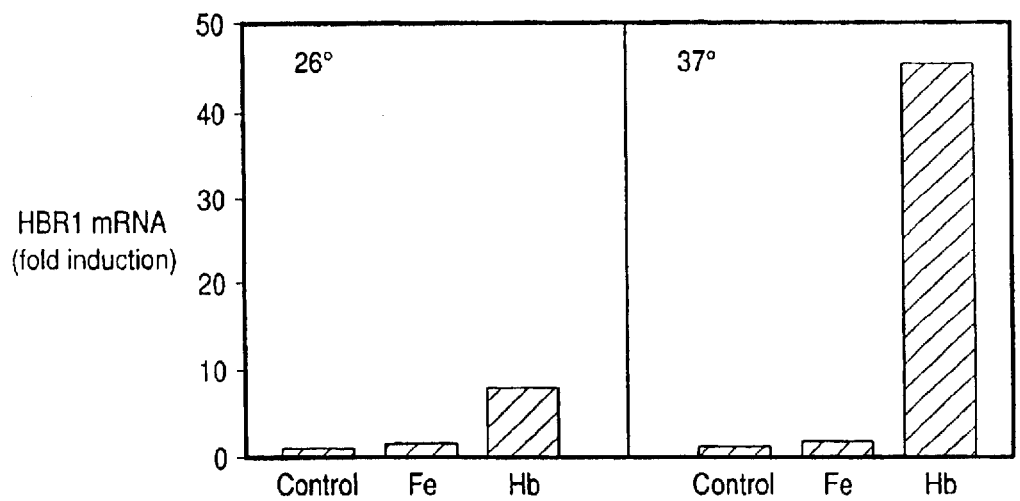

The kinetics of induction of these mRNAs varied both in the time required for maximal induction and the duration of the induced expression (FIG. 1C). HBR1 and HBR2 were transiently induced, but HBR3 expression was sustained beyond 72 h. Although genes that showed reduced expression by RAP-PCR were not systematically examined, we noted that actin expression was suppressed following 24 h growth in hemoglobin (FIG. 1C). Induction of expression was observed at physiological temperatures. Hemoglobin elicited a similar increase in HBR3 expression at either 26° or 37° C. (FIG. 1D). Induction of HBR1 expression, however, was 5-fold greater at 37° than at 26° C. (FIG. 1E).

Example 2

Characterization of Hemoglobin-response Genes

A C. albicans genomic library was screened using probes derived from three cloned ESTs (SEQ ID NOS: 11–13) that were confirmed to be positive by Northern blots. HBR1, HBR2, and HBR3 (SEQ ID NOS: 1–3) are novel genes, each of which showed limited homology to hypothetical proteins of Saccharomyces cerevisiae (Table 1). These genomic clones were mapped to distinct chromosomes (Table 1). Therefore, the hemoglobin-response genes are not physically associated, in contrast to the host-response genes of some pathogenic bacteria which are frequently clustered in pathogenicity islands (3).

TABLE 1

Properties of Hemoglobin-Induced Genes[1]

| Gene | Hemoglobin response | Hyphal response | C. albicans chromosome | S. cerevisiae homologs (% DNA homology) | ORF Features |
|---|---|---|---|---|---|
| HBR1 | +++ | + | 1 SfiI frag S | YDL166C (62%) | ATP/GTP-binding site motif (P loop); phosphorylation sites for PKC, PKA, CK2 |
| HBR2 | ++ | o | 6 SfiI frag C | YFL030W (72%) | pyridoxal phosphate motif |
| HBR3 | +++ | o | 1 SfiI frag E | YOR056C (34%) | |
| HBR4 | ++ | o | | | |
| HBR5 | ++ | o | | | |
| CPY1 | + | + | 7 SfiI frag G | | carboxypeptidase Y |
| Actin | – | | 1 SfiI frag L | | actin |

[1]Properties of 5 novel hemoglobin-inducible ESTs (HBR1–5 and CPY1 are summarized. Induction (+), inhibition (–), or lack of response (o) following growth in 0.1% hemoglobin or hyphal differentiation medium were assessed by Northern blots. Chromosome localization for HBR1, HBR2, and HBR3 was performed using fragments from genomic clones. ESTs for HBR1–HBR5 were searched against the Saccharomyces cerevisiae genome database (http://genome-www.stanford.edu/Saccharomyces/) using FASTA version 3.0t77 (34). Open reading frame motifs were identified using MotifFinder (www.genome.ad.jp).

Example 3

Induction of Hemoglobin-response Genes by Whole Blood

Figure 2A:
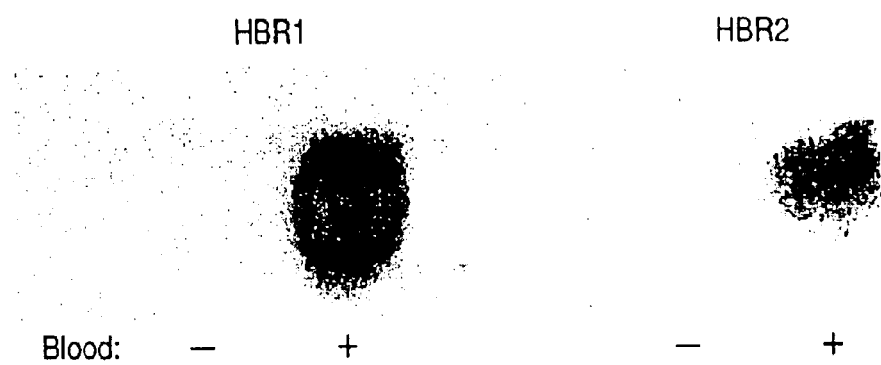
FIGS. 2A–B. Induction of hemoglobin response genes in whole blood. (2A). Cells from C. albicans cultures were resuspended in heparinized rabbit whole blood and allowed to grow at 26° C. for 5 h. Total RNA was extracted from control and treated cells, and expression was determined by Northern analyses. (2B) Hemolytic activity of C. albicans strains 44807 and 32354, which is hemolytic positive control (2, 3) was determined by growing on a Sabouraud dextrose blood plate. Clear zones surrounding the colonies indicate areas of hemolysis.
Figure 2B:

Pathogenic isolates of C. albicans express a hemolysin that could release hemoglobin from erythrocytes when the pathogen gains access to the vascular compartment (23). As predicted from this observation, exposure of C. albicans to whole blood in vitro at 26 or 37° C. for 5 h resulted in rapid induction of HBR1 and HBR2 expression (FIG. 2A). The ATCC 44807 strain used for these experiments was verified to express hemolytic activity following growth on Sabouraud dextrose agar containing rabbit blood and 3% glucose (FIG. 2B). Strain ATCC 32354 was reported previously to produce hemolytic factor (23) and used here as a positive control.

Example 4

Induction of HBR 1 and HBR 3 Expression In Vivo

Figure 3A:
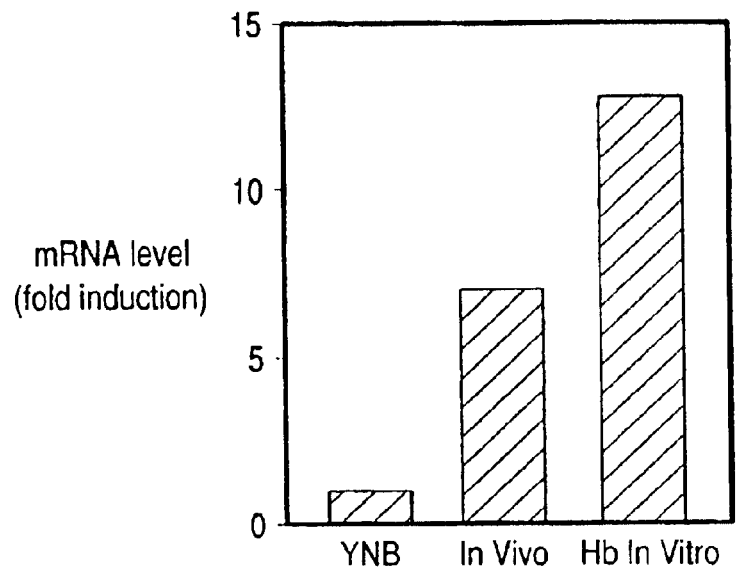
FIGS. 3A–B. Induction of HBR1 and HBR2 expression in vivo in rabbits. C. albicans blastoconidia were injected into Silastic venous catheters implanted into the anterior vena cava of 3 New Zealand white rabbits (26) and incubated in vivo for 5 h before withdrawal for RNA preparation and Northern blots. Representative PhosphorImager analyses of Northern blots show the fold-induction of HBR1 (3A) and HBR3 mRNA expression (3B) for cells recovered from the catheter (in vivo) or parallel cultures maintained in YNB or exposed to 0.1% hemoglobin (Hb) in YNB in vitro.
Figure 3B:
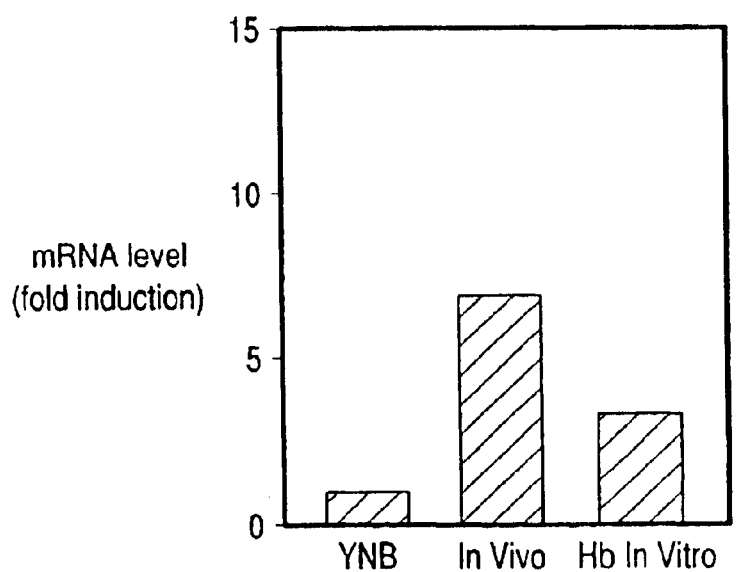

The hemoglobin response genes may also play a role during in vivo pathogenesis of C. albicans, because expression of HBR1 and HBR3 was rapidly induced in a rabbit in vivo model of disseminated candidiasis. C. albicans blastoconidia were incubated for 5 h with heparinized whole blood within the anterior vena cava of rabbits. Induction of mRNAs for both genes was detected following recovery of the cells from the implanted central venous catheter (FIGS. 3A and 3B).

Example 5

Hemoglobin Induction Alters Phosphorylation of Candida Proteins

Figure 4A:
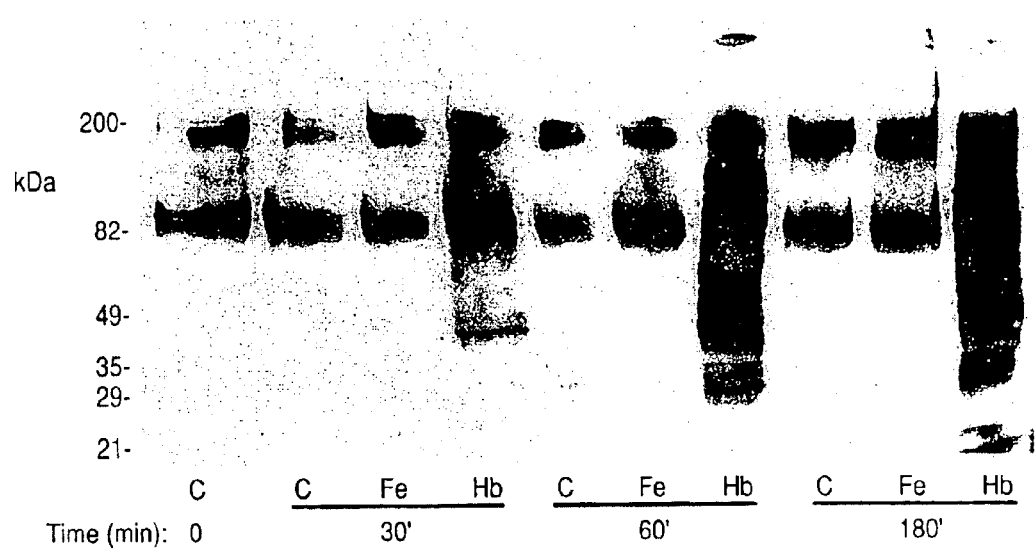
FIGS. 4A–B. Induction of tyrosine phosphorylation by hemoglobin. (4A) C. albicans 44807 cultures growing in YNB were supplemented with ferrous sulfate (Fe) or hemoglobin (Hb) and incubated with rocking at 26° C. At the indicated times, cells lysates were prepared and analyzed by Western blotting using a phosphotyrosine antibody. (4B) Tyrosine phosphorylation induced by hemoglobin in the ura3 mutant CAI4 at 60 min. was compared to that of wild type C. albicans (44807) by Western blotting using the anti-phosphotyrosine antibody RC20.

The effect of hemoglobin induction on tyrosine phosphorylation in C. albicans was also examined. Two proteins with apparent molecular masses of 85 And 160–180 kDa were phosphorylated in control cells, but increased phosphorylation of several proteins at 25–50 kDa was detected at 30 min and reached a maximal level at 60 min. As was seen for the changes in gene expression, the hemoglobin response could not be replicated by exposure of the cells to the same medium containing inorganic iron (FIG. 4A). Therefore tyrosine phosphorylation may be an early event in signaling exposure to hemoglobin following invasion into the vascular compartment.

Example 6

Differentiation Induced by Hemoglobin is Distinct from Hyphal Differentiation

Figure 5A:
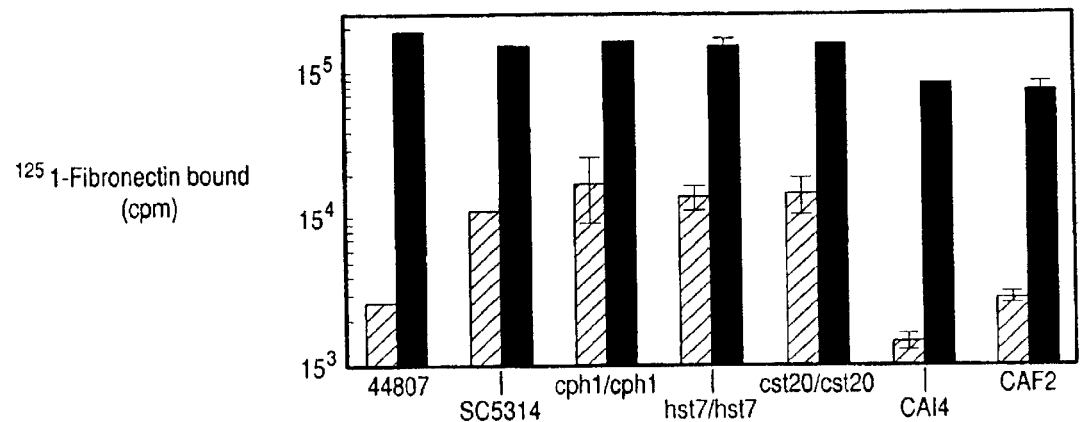
FIGS. 5A–B. Hemoglobin responses in C. albicans mutants impaired in hyphal formation. (5A) $^{125}$I-Fibronectin binding (mean±SD) was measured (20) to each strain after growth in YNB (striped bars) or YNB containing 0.1% hemoglobin (solid bars) for the wild type isolates, ATCC 44807 and SC5314, the URA3+homozygous mutants cph1/cph1, hst7/hst7 and cst20/cst20, the ura3 mutant CAI4, and the corresponding ura3/URA3 parent strain CAF2 (29). (5B) Induction of HBR1 expression by hemoglobin (solid bars) in the ura3 mutant CAI4 was compared to that of wild type C. albicans 44807 and SC5314 by Northern blot analysis. Expression in control cultures without hemoglobin (striped bars) was normalized to 1 and is presented as mean±SD.

To further define the relationship between hyphal differentiation and differentiation induced by hemoglobin, the responses of several C. albicans mutants deficient in hyphal formation were examined. Signal transduction through Cst20p, a homolog of the Ste20p/p65$^{PAK}$ kinases, can trigger hyphal formation in C. albicans (28) and mutants affecting the Cst20 MAP kinase signaling pathway in C. albicans are defective in hyphal formation (19). Three C. albicans mutants defective in this pathway, however, displayed comparable induction of fibronectin binding to their parental isolate SC5314 following growth in medium containing hemoglobin (FIG. 5A). Therefore, the Cst20p/Hst7p pathway is not required for the adhesion response of C. albicans to hemoglobin.

Figure 4B:
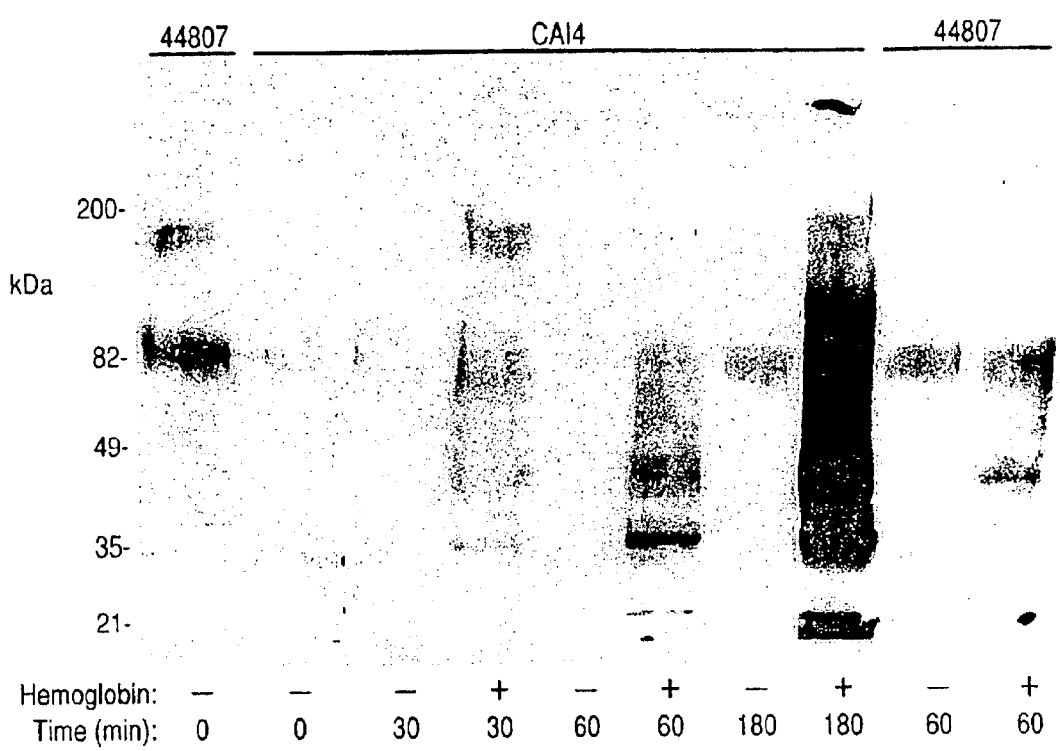
Figure 5B:
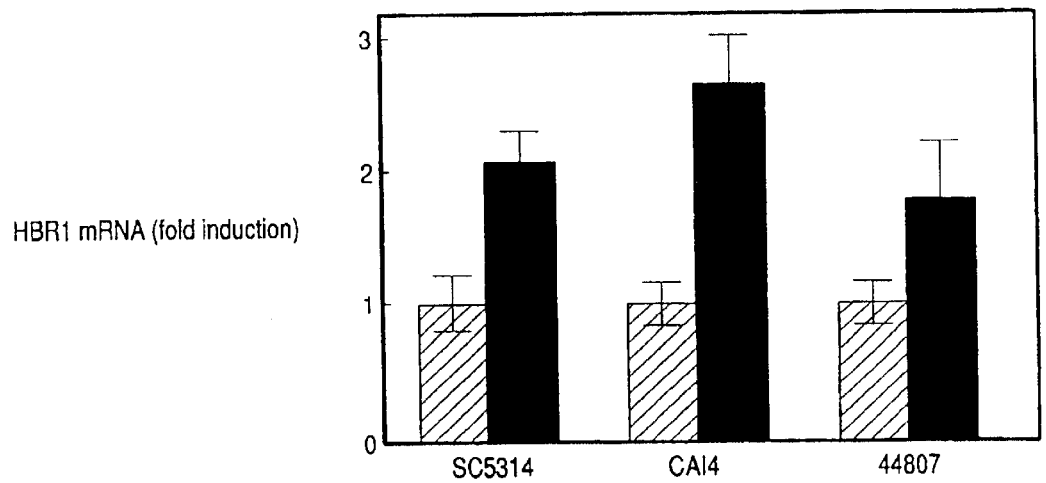

The C. albicans ura3/ura3 mutant strain CAI4 (29) is also derived from SC5314 and is impaired in hyphal formation (19). When maintained serially in Sabouraud broth cultures, this strain failed to respond to hemoglobin by increasing fibronectin binding activity (results no shown), but cultures grown in broth inoculated directly with the CAI4 strain or the ura3/URA3 parent strain (CAF2) grown on Sabouraud agar showed induction of fibronectin binding by hemoglobin (FIG. 5A). The defect in hemoglobin response in the CAI4 mutant when grown serially in broth probably does not involve early events in signaling, since this mutant, when grown serially in broth, showed a similar increase in protein tyrosine phosphorylation as the 44807 isolate following transfer to medium containing hemoglobin (FIG. 4B). Northern blot analyses showed that this strain, when maintained as a serial broth culture, failed to induce HBR1 expression following growth in the presence of hemoglobin (results not shown) but the CAI4 mutant and its parent strain SC5314 both induced HBR1 expression when grown in the same medium innoculated from colonies on solid medium (FIG. 5B). Thus, the induction of HBR1 expression by hemoglobin in strain CAI4 correlates with induction of fibronectin binding.

Discussion

Opportunistic pathogens must recognize specific environments in the host. Some virulence genes remain silent during commensal colonization of environments such as the gastrointestinal tract but become highly expressed when the pathogen reaches a tissue where opportunistic infections can be established. Thus, tissue-specific host factors may be important regulators of virulence gene expression in these organisms. Based on its rapid and pleiotropic effects on protein phosphorylation, cell surface protein expression (22) and gene expression, hemoglobin is a host factor that profoundly alters the phenotype of C. albicans.

Contact of C. albicans with host epithelial cells results in altered tyrosine phosphorylation of several Candida proteins (4). The specific host factors on epithelial cells responsible for this response have not been identified. The phosphorylated proteins induced by hemoglobin differ in molecular weight from those reported for the response of C. albicans to epithelial cell contact (4). These distinct signaling responses suggest that C. albicans can differentially respond to contact with the host epithelia during commensal colonization and exposure to the vascular space in disseminated infections.

The hemolytic factor expressed by pathogenic isolates of C. albicans may enable the cells to acquire iron for maintaining growth (23). The above data demonstrates that expression of this hemolysin can release hemoglobin from whole blood, which in turn alters gene expression and the adhesive phenotype of C. albicans. Although the ability to acquire iron has long been considered an important adaptive response for microbial pathogenesis (30, 31) exposure of Candida to hemoglobin appears to have additional effects on this opportunistic pathogen. The above Examples demonstrate that hemoglobin but not inorganic iron dramatically enhances Candida binding to fibronectin (20) and differentially induces binding to several other extracellular matrix proteins (22). Although iron regulates growth of C. albicans (32), supplementing the growth medium with inorganic iron has no effect on adhesion (20). In addition, hemoglobin induces expression of several surface proteins in the cells grown in defined medium supplemented with hemoglobin. Among these induced surface proteins, fibronectin recognizes a protein with a molecular mass of 55 kDa that is not present in cells grown in the absence of hemoglobin (21, 22). Enhancement of fibronectin binding by hemoglobin is conserved among several pathogenic species in the Candida genus but was not observed in nonpathogenic yeasts or Trichosporon beigelii, which rarely causes disseminated infections (33). Therefore, one role of hemoglobin in the pathogenesis of C. albicans and related species is to regulate interactions with host adhesion molecules. Defining the function of the hemoglobin-response genes may reveal additional pathogenic processes that are induced by hemoglobin.

The above Examples describe the identification of five genes that are preferentially induced by hemoglobin but not by hyphal differentiation. The three genes for which genomic clones were obtained all appear to encode cytoplasmic proteins. Although their functions are unknown, none of the cloned hemoglobin-response genes appears to be the hemoglobin-induced extracellular matrix receptor. The presence of a nucleotide binding P loop in HBR1 suggest that it could be a regulatory protein that mediates some of the phenotypic responses of C. albicans to hemoglobin. Unlike the host-response genes in some bacteria which are clustered in pathogenicity islands, the hemoglobin-response genes in C. albicans appear to be dispersed in the genome. Thus hemoglobin-induced transcription factors and signaling pathways may coordinately regulate the induction of these genes by hemoglobin. Based on the disparate kinetics for their induction, however, a complex signaling pathway may be required to mediate this hemoglobin response.

The process of hyphal differentiation is associated with altered expression of several genes (16, 17). Hyphal differentiation is now recognized as an essential response for pathogenesis of C. albicans, and disruption of several genes required for hyphal differentiation produces avirulent organisms (18, 19). However, the C. albicans MAP kinase mutants that are impaired in hyphal differentiation examined here are not defective in responses to hemoglobin. Our data demonstrate that hemoglobin induces expression of some genes in the hyphal differentiation pathway but does not induce hyphae. However, hemoglobin also induces a second set of genes that are not involved in hyphal differentiation and are rapidly induced both in vitro and in vivo. These genes define a second differentiation pathway that is triggered when C. albicans gains access to the vascular compartment of its host. Future studies will examine the function and expression of these genes during the transition from commensal colonization to disseminated candidiasis.

REFERENCES

1. Guiney, D. G. 1997. Regulation of bacterial virulence gene expression by the host environment. *J Clin Invest.* 99 (4):565–9.
2. Finlay, B. B., and P. Cossart. 1997. Exploitation of mammalian host cell functions by bacterial pathogens. *Science.* 276 (5313):718–25.
3. Falkow, S. 1997. Perspectives series: host/pathogen interactions. Invasion and intracellular sorting of bacteria: searching for bacterial genes expressed during host/pathogen interactions. *J Clin Invest.* 100 (2):239–43.
4. Bailey, A., E. Wadsworth, and R. Calderone. 1995. Adherence of *Candida albicans* to human buccal epithelial cells: host-induced protein synthesis and signaling events. *Infect Immun.* 63 (2):569–72.
5. Pfaller, M. A. 1996. Nosocomial candidiasis: emerging species, reservoirs, and modes of transmission. *Clin Infect Dis.* 22 Suppl 2:S89–94.
6. Pfaller, M. A. 1995. Epidemiology of candidiasis. *J Hosp Infect.* 30 Suppl:329–38.
7. Odds, F. C. 1994. Pathogenesis of *Candida* infections. *J Am Acad Dermatol.* 31:S2–5.
8. Klingspor, L., G. Stintzing, and J. Tollemar. 1997. Deep *Candida* infection in children with leukaemia: clinical presentations, diagnosis and outcome. *Acta Paediatr.* 86 (1):30–6.

9. Hacimustafaoglu, M., B. Ener, O. Tarim, S. Kilic, A. Tanritanir, and I. Ildirim. 1997. Systemic candidiasis with acute Epstein-Barr virus infection. *Acta Paediatr.* 86 (11):1267–70.

10. Tran, L. T., P. Auger, R. Marchand, M. Carrier, and C. Pelletier. 1997. Epidemiological study of *Candida* spp. colonization in cardiovascular surgical patients. *Mycoses.* 40 (5–6):169–73.

11. Nguyen, M. H., J. E. Peacock, Jr., A. J. Morris, D. C. Tanner, M. L. Nguyen, D. R. Snydman, M. M. Wagener, M. G. Rinaldi, and V. L. Yu. 1996. The changing face of candidemia: emergence of non-*Candida albicans* species and antifingal resistance. *Am J. Med.* 100 (6):617–23.

12. Kalya, A. V., and D. G. Ahearn. 1995. Increased resistance to antifingal antibiotics of *Candida* spp. adhered to silicone. *J Ind Microbiol.* 14 (6):451–5.

13. White, T. C., K. A. Marr, and R. A. Bowden. 1998. Clinical, cellular, and molecular factors that contribute to antifungal drug resistance. *Clin Microbiol Rev.* 11 (2):382–402.

14. Marr, K. A., T. C. White, J. A. van Burik, and R. A. Bowden. 1997. Development of fluconazole resistance in *Candida albicans* causing disseminated infection in a patient undergoing marrow transplantation. *Clin Infect Dis.* 25 (4):908–10.

15. Prasad, R., S. K. Murthy, V. Gupta, and R. Prasad. 1995. Multiple drug resistance in *Candida albicans. Acta Biochim Pol.* 42 (4):497–504.

16. Newport, G., and N. Agabian. 1997. KEX2 influences *Candida albicans* proteinase secretion and hyphal formation. *J. Biol. Chem.* 272 (46):28954–61.

17. Bailey, D. A., P. J. Feldmann, M. Bovey, N. A. Gow, and A. J. Brown. 1996. The *Candida albicans* HYR1 gene, which is activated in response to hyphal development, belongs to a gene family encoding yeast cell wall proteins. *J Bacteriol.* 178 (18):5353–60.

18. Lo, H. J., J. Köhler, B. DiDomenico, D. Loebenberg, A. Cacciapuoti, and G. R. Fink. 1997. Nonfilamentous *C. albicans* Mutants Are Avirulent. *Cell.* 90:939–949.

19. Köhler, J. R., and G. R. Fink. 1996. *Candida albicans* strains heterozygous and homozygous for mutations in mitogen-activated protein kinase signaling components have defects in hyphal development. *PNAS.* 93:13316–13320.

20. Yan, S., E. Negre, J. A. Cashel, N. Guo, C. A. Lyman, T. J. Walsh, and D. D. Roberts. 1996. Specific induction of fibronectin binding activity by hemoglobin in *Candida albicans* grown in defined media. *Infect Immun.* 64:2930–5.

21. Yan, S., R. G. Rodrigues, and D. D. Roberts. 1998. Hemoglobin-induced binding of *Candida albicans* to the cell-binding domain of fibronectin Is independent of the Arg-Gly-Asp sequence. *Infect Immun.* 66:1904–1909.

22. Yan, S., R. G. Rodrigues, D. Cahn-Hidalgo, T. J. Walsh, and D. D. Roberts. 1998. Hemoglobin induces binding of several extracellular matrix proteins to *Candida albicans*, Identification of a common receptor for fibronectin, fibrinogen and laminin. *J. Biol. Chem.* 273 (10):5638–5644.

23. Manns, J. M., D. M. Mosser, and H. R. Buckley. 1994. Production of a hemolytic factor by *Candida albicans. Infect Immun.* 62:5154–5156.

24. Negre, E., T. Vogel, A. Levanon, R. Guy, T. J. Walsh, and D. D. Roberts. 1994. The collagen binding domain of fibronectin contains a high affinity binding site for *Candida albicans. J. Biol. Chem.* 269:22039–45.

25. Chu, W. S., B. B. Magee, and P. T. Magee. 1993. Construction of an SfiI macrorestriction map of the *Candida albicans* genome. *J. Bacteriol.* 175 (20):6637–6651.

26. Walsh, T. J., J. Bacher, and P. A. Pizzo. 1988. Chronic silastic central venous catheterization for induction, maintenance and support of persistent granulocytopenia in rabbits. *Lab Anim Sci.* 38 (4):467–71.

27. Mukhtar, M., D. A. Logan, and N. F. Kaufer. 1992. The carboxypeptidase Y-encoding gene from *Candida albicans* and its transcription during yeast-to-hyphae conversion. *Gene.* 121 (1):173–7.

28. Leberer, E., D. Harcus, I. D. Broadbent, K. L. Clark, D. Dignard, K. Ziegelbauer, A. Schmidt, N. A. Gow, A. J. Brown, and D. Y. Thomas. 1996. Signal transduction through homologs of the Ste20p and Ste7p protein kinases can trigger hyphal formation in the pathogenic fungus *Candida albicans. Proc Natl Acad Sci U.S.A.* 93 (23):13217–22.

29. Fonzi, W. A., and M. Y. Irwin. 1993. Isogenic strain construction and gene mapping in *Candida albicans. Genetics.* 134:717–728.

30. Esterly, N., S. Brammer, and R. Crounse. 1967. The relationship of transferrin and iron to serum inhibiton of *Candida albicans. J invest Dermatol.* 49:437–442.

31. Weinberg, E. 1978. Iron and Infection. *Microbiol Rev.* 42:45–66.

32. Moors, M., T. Stull, K. Blank, H. Buckley, and D. Mosser. 1992. A role for complement receptor-like molecules in iron acquisition by *Candida albicans. J Exp Med.* 175:1643–1651.

33. Rodrigues, R, S. YAN, T. Walsh, and D. Roberts. 1998. Hemoglobin differentially induces binding of *Candida, Trichosporon*, and *Saccharomyces* Species to fibronectin. *J Infect Dis.*

34. Pearson, W. R., and D. J. Lipman. 1988. Improved tools for biological sequence comparison. *Proc Natl Acad Sci U.S.A.* 85 (8):2444–8.

What is claimed is:

1. An isolated nucleic acid molecule which encodes a protein having SEQ ID NO:4.

2. The nucleic acid molecule of claim 1, wherein said nucleic acid molecule has a nucleotide sequence according to SEQ ID NO:1.

3. A vector comprising the nucleic acid molecule of claim 1.

4. An isolated cell comprising the vector of claim 3.

5. A method for producing a protein encoded by SEQ ID NO. 1, said method comprising growing the cell of claim 4 under conditions such that the encoded protein is produced.

6. A nucleic acid probe comprising an oligonucleotide having a sequence of at least 200 contiguous nucleotides of (i) the nucleic acid molecule of claim 1 or (ii) the complement of such nucleic acid molecule.

7. A kit for detecting *Candida albicans* in a sample comprising the nucleic acid probe of claim 6.

8. An isolated nucleic acid molecule which encodes a protein having SEQ ID NO:5.

9. The nucleic acid molecule of claim 8, wherein said nucleic acid molecule has a nucleotide sequence according to SEQ ID NO:2.

10. A vector comprising the nucleic acid of molecule of claim 8.

11. An isolated cell comprising the vector of claim 10.

12. A method for producing a protein encoded by SEQ ID NO. 2, said method comprising growing the cell of claim 11 under conditions such that the encoded protein is produced.

13. A nucleic acid probe comprising an oligonucleotide having a sequence of at least 200 contiguous nucleotides of (i) the nucleic acid molecule of claim 8 or (ii) the complement of such nucleic acid molecule.

14. A kit for detecting *Candida albicans* in a sample comprising the nucleic acid probe of claim 13.

15. An isolated nucleic acid molecule comprising a nucleotide sequence according to SEQ ID NO:3.

16. A vector comprising the nucleic acid of molecule of claim 15.

17. An isolated cell comprising the vector of claim 16.

18. A method for producing a protein encoded by SEQ ID NO. 3, said method comprising growing the cell of claim 17 under conditions such that the encoded protein is produced.

19. A nucleic acid probe comprising an oligonucleotide having a sequence of at least 200 contiguous nucleotides of (i) the nucleic acid molecule of claim 15 or (ii) the complement of such nucleic acid molecule.

20. A kit for detecting *Candida albicans* in a sample comprising the nucleic acid probe of claim 19.

* * * * *

SEQUENCE LISTING

<160> NUMBER OF SEQ ID NOS: 13

<210> SEQ ID NO 1
<211> LENGTH: 1347
<212> TYPE: DNA
<213> ORGANISM: Candida albicans

<400> SEQUENCE: 1

```
tcaagtccaa accacattta cttatatctt gaccaagggc aaaattggaa tatsrsacct        60
```

```
csytccattt  aaaccaaggg  ggttcaaccc  tggcattcca  tattaacyta  atcttttttc     120
tgggcggtag  cgtagawgac  accatgtttg  ctgattttct  akgaatagta  gttgstgaat     180
tcccaacaaa  cagaacaaaa  aaaaaaagtc  ttgcaaacga  gagtgagaga  aagaaaacaa     240
aaaaaaattc  tagaagattt  ttcttttaat  aggcaacctc  aaattgcaca  tctcatcact     300
atgacaacca  tgtcaagaag  atatacacca  aacataatta  taacaggtac  acctgggtgt     360
gggaaatcat  ctcattccct  gagtttagtt  tctcaactca  atcaaactct  tggtaaagag     420
acgacgattc  atttcaagca  ctttaatatc  agtgaaatag  caaaggaaag  agactgcatt     480
gaatcttatg  atgccaagtt  agatacttcg  attgtagacg  aagacaaatt  gctagactcg     540
ttagagcctg  atttggaaaa  ggggggagtg  gtcgttgatt  ggcattgttg  tgatattttc     600
ccagaaagat  taattgattt  ggtggttgta  ttgcgtacag  acaattccaa  tttgtttgat     660
cgattaaaga  ctagaaacta  caatgatcta  aaattacaag  aaaacttgga  ttgtgagatc     720
atggaagtga  tattacaaga  agcaaaggac  agctatattc  ctgacatagt  aattgagttg     780
cgttcagaca  cagctgaaga  gatggatgaa  aacgttgata  gaataagctc  ttgggtggaa     840
acatggatag  aggaccatcc  agatgggggtt  agcaatgaat  tgaacaagca  atataaccca     900
gatgattctt  ctgatgaagg  tgatgacaac  agcgattccg  atgaatatga  acttgaagaa     960
gacgaacaag  aagaagagga  ggaaagagaa  gagtacgatg  aagagaccaa  tgaagagatg    1020
gagcatacag  aagatattgc  acaatagaaa  aggcatatat  tatctaaatt  aatgtacaga    1080
agttttcata  agtgttttta  tttttttatt  taggttaatt  tattgacaac  tcttcttaag    1140
tagatcaaag  ccaacaaaga  gaaaagtacc  aaggcagcat  agtagcctct  tgtcactaag    1200
aaatatgtcc  aagtacccga  aagtttgtcc  atgttgtgtt  tttctaattc  agccacacat    1260
ttaacgtcat  gttcgaaaat  gtattttgat  tcttcaatga  tttccaactt  tgttcttcc     1320 gtcaaaccat  ttcttgtcac  caactcg                                           1347
```

<210> SEQ ID NO 2
<211> LENGTH: 3250
<212> TYPE: DNA
<213> ORGANISM: Candida albicans
<220> FEATURE:
<221> NAME/KEY: unsure
<222> LOCATION: (14)
<223> OTHER INFORMATION: The "n" at position 14 can be either A, T, G or C.
<220> FEATURE:
<221> NAME/KEY: unsure
<222> LOCATION: (55)
<223> OTHER INFORMATION: The "n" at position 55 can be either A, T, G, or C.
<220> FEATURE:
<221> NAME/KEY: unsure
<222> LOCATION: (163)
<223> OTHER INFORMATION: The "n" at position 163 can be either A, T, G, or C.
<220> FEATURE:
<221> NAME/KEY: unsure
<222> LOCATION: (436)
<223> OTHER INFORMATION: The "n" at position 436 can be either A, T, G, or C.
<220> FEATURE:
<221> NAME/KEY: unsure
<222> LOCATION: (3210)
<223> OTHER INFORMATION: The "n" at position 3210 can be either A, T, G, or C.

<400> SEQUENCE: 2

```
ttttaaaagt  tatngggatt  atatgaatac  catagttgat  aaaaacataa  attanacctt      60
```

```
tagtccttct atcaaatagt tctggttaat ccaccagttt gtcgacttaa atgaaattgt       120
aaatccatat ttaataattt aacaaatgta ttataagcaa ttngaggaat tgccagttgg       180
gcaacaacta gcaaaaatgg cattaacgta attctccaaa taataacagc accaaatcgg       240
agctccacca taagctaaaa ttaaactttc ctataacggt cagaaatacc ccgacttcat       300
tagtccaatc aatattcatc gtatcaatam ttykwwkram awammmkgkw mywksmacaa       360
ttctwracca twttgkyamm aamkratwry swtaatttgg cmcaykatww stmgmakttt       420
gmrattwara ttawtntttc ggccaaatgg ttttaaataa tgatttcamc ataaatgatt       480
cactatttkc gctactacta ctaccactac tagtagtatc attatcttgt attggtggtt       540
ttaccttggg tggaggtttc agtaatgttt tgggtgttgt ctttgaagtc gaagtcgaag       600
tcgaagtcga agtcgatttt aatgatgatg atgatgaagt tgatttgaaa ttagaagttg       660
atttattagt gaaatatcta atacttgata ttttaattga tctagaaata ggaaaactaa       720
aaggtattgg tgatataaac ctcacgggag atggttttat caatttaaca tttctaataa       780
acatctatga tattgtgtgt gtctgtgtat gttgactagt aagtaattga gttggattga       840
ttctgaactc aaataaagga ggaggggggag tatggttata acaaaaattg tgattctaat       900
caaagtatac aatgaataaa tatataaaag gaaggtgatg gcaatgataa agtgaaaatg       960
aaattgaaaa tggaagtaat tatatataaa tgaaagaaaa ttaaagtgt ggcatcctat      1020 tcggtcggac aatttttctc tttcaaactt cttgttgatt gttgtaactt ttaattttgt      1080
atggggtcag gatttagtgt atgtttctct gactcattta aaaagaatc cttttgcgga       1140 tttcggaagc gacttcttaa tatgttatcc catatatgtc attagtatca tcaatgctag      1200 aaagattaa taaacctact ggttgagtag ttttagagta aattaatttg caacagctct       1260
tcataataat tgatcactgt ggaaggtatt agttttgtca ttcgggggc taacatttga       1320 aagacatcca actatctcta accccataga agaactgttg tcattgcaga tatgtgttat      1380
aaatcagaaa tatatatata tgtatataag ttcatttatt tatatatcac ttttgcataa      1440
atatctagtg acctaaattc aattactaaa ttgcttattt caattcattt aatgattctt      1500
caagagcttt agttaattta tcaacatgac cagcataaac tgaataaccc atatgaccaa      1560
ctctaaagta tttaccaact aatttcttat ggatacctcc agcaacaaca aaacctttt       1620 cagataattt tttcaataaa tcaggtccat tgattccatc agggaaata aactgcagtt       1680 aatccatgag cagcaacttt atgatcaaca ggcaagattt ttaaacccaa cttttcaaca      1740
ttagatttga atttatcaga aacttgagca tgtttagcaa atctttcatc aattggttga      1800
ctcaaaattt catctaatga agttttaaa gcagtaatgg tttgaacagc tggagtagca      1860
aaataagcac cattgccatt tcataagct ttcataattg gtgtccatct ctttaaagat      1920
gcaaaaaaag ttgattcctt ttctttattt aaagctttag ctaaagctct ttcactggca      1980
taaaaaattg ataaacctgc tggaacacca atagcctttt gagatgcagt caaagcaaaa      2040
tcaatacccc atttatcaaa ttctaaatct tcaacagcaa tagaacaaac cccatcaaca      2100
ataattaaag tatcaggaga aactttttaa caactttact aatggcttca acatcactaa      2160
ctacagaart wgaagtatca acatgagtta tagtaatggc agaatatttt tccytttgta      2220
attgttgctc aattttatcc aatggaacaa catcaccaac ttcagctgtc aatacatcaa      2280
catcagctcc ataaacttta agacattcca gcaaatgaat cagagaaaaa tccagtactt      2340
aaaactaaaa cttttttcacc tggattcaac aaattacttg aagcaacatc ccaacccaaa      2400
gtacctgatc cactcaatac ataaccttga gtattggtat cagtgggatt taaatacttt      2460
```

-continued

```
tctcaaactt ttcaacactg attgggaaag tagaaatgaa ttctggtgaa agtatgagct    2520
tgtgaaggtg ttgccattga tgccaaaaca tcatcagaaa aattcaattg gaccagggat    2580
taaagtcaat ttatattcag gttgtttata ttggaaaaac attttattgt tattggtgtt    2640
gaataaatta rtcgtartar ttgaaattga wttaaaattt gttaaagaaa ttggtttaat    2700
taatttataa ttgaatttat tgattattac ttttgaagtt gttaatgttt taaacattca    2760
aaagaataaa aataaaaagt aattgaatag ttattacttg gtgtatgtaa agaagtaaaa    2820
gaaagaaaga aagaaataaa gaaagagta ttaaaaaaat ttcaaatatt taaaagaaga    2880
aggagaagga gagacaatca ttttttatcg ttgttgttgt tgttgttgtt tgttgttgat    2940
taataatatt attagttagg atggagagag agagagagag agagtcctat aagaccaatg    3000
ggaaagtctg gagaaacgga acttttcctt ttttctttct ttctttcttt cttttggta    3060 gctcttttga ttgcttcaaa aactctctct ctctctctct tctccccct ccccgccacc    3120 acgactacta ctactactac tattactact attactgccc actaccacta ccaccaccac    3180 taccttgtt atccatttt tgttccgacn aaaactttt tctttcccgg ttttttttt      3240 atcgtccgcc                                                           3250
```

<210> SEQ ID NO 3
<211> LENGTH: 1428
<212> TYPE: DNA
<213> ORGANISM: Candida albicans
<220> FEATURE:
<221> NAME/KEY: unsure
<222> LOCATION: (1053)
<223> OTHER INFORMATION: The "n" at position 1053 can be either A, T, G or C.
<220> FEATURE:
<221> NAME/KEY: unsure
<222> LOCATION: (1314)
<223> OTHER INFORMATION: The "n" at position 1314 can be either A, T, G or C.

<400> SEQUENCE: 3

```
tccaaatttg ttcctgaatg acccgaaaaa cagattccat caatcattct cggccgggtc     60
agtgttgacg cgtggggaag ggaaaggaaa gaaagaaaaa ataactcwtt caactgggtg    120
taaggaagca ggaaggaatc atttagttca acgggataaa attcgtgtgc aactcaaatt    180
ggcggggaaa ttgtgcagca atggaaaaaa ggatctcata ctagatttac actcacttta    240
acaaactaac aaacaattga gtgttggtwa cattttttt ttgttttttg gtctttgtgt    300
ttagtttctt ttgttggtta tctttgtaaa aaatgcttat caggaattaa acaatatgaa    360
actttacaaa ctggggagag ttcaaaaaaa ctgatataaa tggggaaggt ttttgctcca    420
aatgtttttt gaattgattt ttgttttgc ttttttgttt tacttttcc tccagctatt     480 ataacaattt taatatcact ttctactact attcaaaata atgtgtaaaa ctgaaatttg    540
cggaatttgt cgtatgtgat tgctcctagc ttttattgaa ttgattcact tttaactgtt    600
caatgatact aacatcaaga atttttaatt tagaacataa atcttggacc ggttgtggta    660
aacatgtcca cgaaataatg gatatcagtt ctaaagataa ttggtgtacc tgtgagccat    720
tggataaaga tgaagaagtt ttcattgaag gtcatgggt ttatccacca aaagcaggtc     780
aaggtttgag aagaggcagt ggttgcggtt accagagttc ttccccaaga taaataagaa    840
cgtctgcgat gaatcgtgas gttaggttgt tgttgttttt tttttattgc aaaattaaaa    900
agttaattta ttggtttggt gctggtattc caaatagtta gtattgtttt acatagaaaa    960
```

```
tatatttaaa catattcagg ttttttggga ggtgttgatt tgtggacact acatgtadra    1020
gcgttgttga tattggggtt atattcggaa ganaactaaa attgcaaaac gtaactgttg    1080
ttattgagca cttgccagtt gatactctta cctacagttg acctttaat gctaggttag     1140 tttatgacct ttttccaatc tacaagtgga agataataat ttaaagacga attcttggag    1200
ttgagcaaaa gcttttggt agctgttgaa atttgctatt gcccttgtgc cgcaaataca     1260
ascctacaaa ctcaaggtgt twagcccaat aacgtgttgt cttaaacgtt tganctagtc    1320
ttctatttag aatgcctgac aattaagtta aattttgatt gtgagctcaa cagatgttct    1380
atcctactca catggcccgt atattgttgc gaatttgcga atgttcac                 1428
```

<210> SEQ ID NO 4
<211> LENGTH: 248
<212> TYPE: PRT
<213> ORGANISM: Candida albicans

<400> SEQUENCE: 4

```
Met Thr Thr Met Ser Arg Arg Tyr Thr Pro Asn Ile Ile Ile Thr Gly
  1               5                  10                  15

Thr Pro Gly Cys Gly Lys Ser Ser His Ser Leu Ser Leu Val Ser Gln
             20                  25                  30

Leu Asn Gln Thr Leu Gly Lys Glu Thr Thr Ile His Phe Lys His Phe
         35                  40                  45

Asn Ile Ser Glu Ile Ala Lys Glu Arg Asp Cys Ile Glu Ser Tyr Asp
     50                  55                  60

Ala Lys Leu Asp Thr Ser Ile Val Asp Glu Asp Lys Leu Leu Asp Ser
 65                  70                  75                  80

Leu Glu Pro Asp Leu Glu Lys Gly Gly Val Val Val Asp Trp His Cys
                 85                  90                  95

Cys Asp Ile Phe Pro Glu Arg Leu Ile Asp Leu Val Val Val Leu Arg
            100                 105                 110

Thr Asp Asn Ser Asn Leu Phe Asp Arg Leu Lys Thr Arg Asn Tyr Asn
        115                 120                 125

Asp Leu Lys Leu Gln Glu Asn Leu Asp Cys Glu Ile Met Glu Val Ile
    130                 135                 140

Leu Gln Glu Ala Lys Asp Ser Tyr Ile Pro Asp Ile Val Ile Glu Leu
145                 150                 155                 160

Arg Ser Asp Thr Ala Glu Glu Met Asp Glu Asn Val Asp Arg Ile Ser
                165                 170                 175

Ser Trp Val Glu Thr Trp Ile Glu Asp His Pro Asp Gly Val Ser Asn
            180                 185                 190

Glu Leu Asn Lys Gln Tyr Asn Pro Asp Asp Ser Asp Glu Gly Asp
        195                 200                 205

Asp Asn Ser Asp Ser Asp Glu Tyr Glu Leu Glu Glu Asp Glu Gln Glu
    210                 215                 220

Glu Glu Glu Glu Arg Glu Glu Tyr Asp Glu Glu Thr Asn Glu Glu Met
225                 230                 235                 240

Glu His Thr Glu Asp Ile Ala Gln
                245
```

<210> SEQ ID NO 5
<211> LENGTH: 287
<212> TYPE: PRT
<213> ORGANISM: Candida albicans

<400> SEQUENCE: 5

```
Met Phe Gln Tyr Lys Gln Pro Glu Tyr Lys Leu Thr Leu Ile Pro
 1               5                  10                  15

Gly Pro Ile Asn Phe Ser Asp Asp Val Leu Ala Ser Met Ala Thr Pro
             20                  25                  30

Ser Gln Ala His Thr Ser Pro Glu Phe Ile Ser Thr Phe Gln Ser Val
         35                  40                  45

Leu Lys Ser Leu Arg Lys Val Phe Lys Ser Thr Asn Thr Gln Gly
     50                  55                  60

Tyr Val Leu Ser Gly Ser Gly Thr Leu Gly Trp Asp Val Ala Ser Ser
 65              70                  75                  80

Asn Leu Leu Asn Pro Gly Glu Lys Val Leu Val Leu Ser Thr Gly Phe
                 85                  90                  95

Phe Ser Asp Ser Phe Ala Gly Met Ser Lys Val Tyr Gly Ala Asp Val
             100                 105                 110

Asp Val Leu Thr Ala Glu Val Gly Asp Val Pro Leu Asp Lys Ile
             115                 120                 125

Glu Gln Gln Leu Gln Arg Glu Lys Tyr Ser Ala Ile Thr Ile Thr His
         130                 135                 140

Val Asp Thr Ser Thr Ser Val Val Ser Asp Val Glu Ala Ile Lys Val
145                 150                 155                 160

Val Lys Lys Val Ser Pro Asp Thr Leu Ile Ile Val Asp Gly Val Cys
                 165                 170                 175

Ser Ile Ala Val Glu Asp Leu Glu Phe Asp Lys Trp Gly Ile Asp Phe
             180                 185                 190

Ala Leu Thr Ala Ser Gln Lys Ala Ile Gly Val Pro Ala Gly Leu Ser
         195                 200                 205

Ile Phe Tyr Ala Ser Glu Arg Ala Leu Ala Lys Ala Leu Asn Lys Glu
         210                 215                 220

Lys Glu Ser Thr Phe Phe Ala Ser Leu Lys Arg Trp Thr Pro Ile Met
225                 230                 235                 240

Lys Ala Tyr Glu Asn Gly Asn Gly Ala Tyr Phe Ala Thr Pro Ala Val
             245                 250                 255

Gln Thr Ile Thr Ala Leu Lys Thr Ser Leu Asp Glu Ile Leu Ser Gln
             260                 265                 270

Pro Ile Asp Glu Arg Phe Ala Lys His Ala Gln Val Ser Asp Lys
         275                 280                 285

<210> SEQ ID NO 6
<211> LENGTH: 18
<212> TYPE: DNA
<213> ORGANISM: Candida albicans

<400> SEQUENCE: 6
aatctagagc tcctcctc                                              18

<210> SEQ ID NO 7
<211> LENGTH: 18
<212> TYPE: DNA
<213> ORGANISM: Candida albicans

<400> SEQUENCE: 7
aatctagagc tccagcag                                              18

<210> SEQ ID NO 8
<211> LENGTH: 18
<212> TYPE: DNA
```

```
<213> ORGANISM: Candida albicans

<400> SEQUENCE: 8
aatctagagc tctcctgg                                                    18

<210> SEQ ID NO 9
<211> LENGTH: 18
<212> TYPE: DNA
<213> ORGANISM: Candida albicans

<400> SEQUENCE: 9
aatctagagc tctccagc                                                    18

<210> SEQ ID NO 10
<211> LENGTH: 18
<212> TYPE: DNA
<213> ORGANISM: Candida albicans

<400> SEQUENCE: 10
aatctagagc tccctcca                                                    18

<210> SEQ ID NO 11
<211> LENGTH: 399
<212> TYPE: DNA
<213> ORGANISM: Candida albicans
<220> FEATURE:
<221> NAME/KEY: unsure
<222> LOCATION: (204)
<223> OTHER INFORMATION: The "n" at position 204 can be either A, T, G
      or C.
<220> FEATURE:
<221> NAME/KEY: unsure
<222> LOCATION: (225)
<223> OTHER INFORMATION: The "n" at position 225 can be either A, T, G
      or C.

<400> SEQUENCE: 11
cacacgcaca cggaagaaga ggaggaaaga gaagagtacg atgaagagac caatgaagag        60
atggagcata cagaagatat tgcacaatag aaaaggcata tattatctaa attaatgtac       120
agaagttttc ataagtgttt ttattttttt atttaggtta atttattgac aactcttctt       180
aagtagatca aagccaacaa aganaaaagt accaaggcag catantagcc tcttgtcact       240
aagaaatatg tccaagtacc cgaaagtttg tccatgttgt gttttctaa ttcagccaca        300 catttaacgt catgttcgaa aatgtatttt gattcttcaa tgatttccaa cttttgttct       360
tccgtgtgcg ttgtgatttg ttcttcccgt gtggtgtaa                             399

<210> SEQ ID NO 12
<211> LENGTH: 270
<212> TYPE: DNA
<213> ORGANISM: Candida albicans
<220> FEATURE:
<221> NAME/KEY: unsure
<222> LOCATION: (158)
<223> OTHER INFORMATION: The "n" at position 158 can be either A, T, G
      or C.
<220> FEATURE:
<221> NAME/KEY: unsure
<222> LOCATION: (173)
<223> OTHER INFORMATION: The "n" at position 173 can be either A, T, G
      or C.
<220> FEATURE:
<221> NAME/KEY: unsure
<222> LOCATION: (236)
<223> OTHER INFORMATION: The "n" at position 236 can be either A, T, G
      or C.
<220> FEATURE:
```

```
<221> NAME/KEY: unsure
<222> LOCATION: (249)
<223> OTHER INFORMATION: The "n" at position 249 can be either A, T, G
      or C.
<220> FEATURE:
<221> NAME/KEY: unsure
<222> LOCATION: (251)
<223> OTHER INFORMATION: The "n" at position 251 can be either A, T, G
      or C.

<400> SEQUENCE: 12
aatctagagc tctccagcaa caacaaaacc tttttcagat aattttttca ataaatcagg      60
tccattgatt ccatcaggga aataaactgc tgttaatcca tgagcagcaa ctttatgatc    120
aacaggcaag atttttaaac ccaactttc aacattanat ttgaatttat canaaacttg    180
agcatgttta gcaaatcttt catcaattgg ttgactcaaa atttcatcta atgaantttt    240
ttaaagcant natggttttg aacacctgga                                     270

<210> SEQ ID NO 13
<211> LENGTH: 351
<212> TYPE: DNA
<213> ORGANISM: Candida albicans
<220> FEATURE:
<221> NAME/KEY: unsure
<222> LOCATION: (124)
<223> OTHER INFORMATION: The "n" at position 124 can be either A, T, G
      or C.

<400> SEQUENCE: 13
ggcttaatct agagctctcc agcaccaaac caataaatta actttttaat tttgcaataa     60
aaaaaaaaca acaacaacct aacgtcacga ttcatcgcag acgttcttat ttatcttggg    120
gaanaactct ggtaaccgca accactgcct cttctcaaac cttgacctgc ttttggtgga    180
taaaccccat gaccttcaat gaaaacttct tcatctttat ccaatggctc acaggtacac    240
caattatctt tagaactgat atccattatt tccgtggaca tgtttaccac aaccggtcca    300
agatttatgt ttgacaaatt cccgcaaatt tcaagttta cacattgttt t              351
```